US006220863B1

(12) United States Patent
Kamohara et al.

(10) Patent No.: US 6,220,863 B1
(45) Date of Patent: Apr. 24, 2001

(54) ROOT CANAL FILLING MATERIAL

(75) Inventors: Hiroshi Kamohara; Nobutaka Watanabe; Masao Abiru, all of Tokyo (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 09/488,751

(22) Filed: Jan. 21, 2000

(30) Foreign Application Priority Data

Feb. 15, 1999 (JP) .................................... 11-036137

(51) Int. Cl.$^7$ ....................................... A61C 5/02
(52) U.S. Cl. ............................. 433/224; 523/116
(58) Field of Search ................... 433/224, 228.1; 106/35; 523/116, 117

(56) References Cited

U.S. PATENT DOCUMENTS

| 4,483,679 | * | 11/1984 | Fujisawa et al. ..................... 433/228 |
| 4,550,030 | | 10/1985 | Ohi et al. . |
| 4,604,142 | | 8/1986 | Kamohara et al. . |
| 4,768,951 | | 9/1988 | Abiru et al. . |
| 4,814,011 | | 3/1989 | Kamohara et al. . |
| 4,838,789 | | 6/1989 | Tanaka et al. . |
| 4,909,847 | | 3/1990 | Ohi et al. . |
| 4,911,759 | | 3/1990 | Ohi et al. . |
| 4,931,096 | * | 6/1990 | Fujisawa et al. ..................... 106/35 |
| 4,959,220 | | 9/1990 | Yamamoto et al. . |
| 4,986,754 | * | 1/1991 | Chang et al. ......................... 433/224 |
| 5,051,130 | * | 9/1991 | Futami et al. ......................... 106/35 |
| 5,203,914 | | 4/1993 | Futami et al. . |
| 5,631,320 | | 5/1997 | Kamohara et al. . |
| 5,637,628 | | 6/1997 | Kamohara et al. . |
| 5,698,610 | | 12/1997 | Futami et al. . |
| 5,907,002 | | 5/1999 | Kamohara et al. . |

* cited by examiner

*Primary Examiner*—John J. Wilson
*Assistant Examiner*—Melba Bumgarner
(74) *Attorney, Agent, or Firm*—Oblon, Spivak, McClelland, Maier & Neustadt, P.C.

(57) ABSTRACT

A root canal filling material is disclosed, including (A) from 1 to 50% by weight of guttapercha and/or trans-polyisoprene, (B) from 0.1 to 10%, by weight of polybutene having a number average molecular weight of from 600 to 4,000, (C) from 0.1 to 10% by weight of ester gum, (D) from 0.1 to 20%, by weight of paraffin wax, and (E) from 10 to 95% by weight of one or two or more inorganic fillers selected from zinc oxide, barium sulfate and calcium hydroxide. The root canal filling material of the invention has high adhesion to root canal walls and a sufficient working time and can be used in a method of filling a root canal upon heat softening during the root canal treatment.

1 Claim, No Drawings

ROOT CANAL FILLING MATERIAL

BACKGROUND OF THE INVENTION

1. Field of the Invention

The present invention relates to a root canal filling material that is used for dental remedies and to a method for filling a root canal upon heat softening during the root canal treatment. In particular, the invention relates to a root canal filling material with improved filling operability and adhesion to root canal walls.

2. Description of the Background

As to the matter of remedies for dental pulp disease and apical periodontitis, normally in root canal treatment, a root canal filling material is employed which is a substance which is not only materially safe, but which is also safe to living bodies upon filling a root canal after extirpation of the dental pulp, thereby keeping a tooth root harmless against periodontal tissue. There are many variations of root canal filling material. Of these, most frequently used is a thin needle-like root canal filling material called a guttapercha point. In general, a guttapercha point is comprised of guttapercha as a natural resin and zinc oxide as the major components. A root canal is filled with the material after extirpation of dental pulp.

In order to fill a root canal with a guttapercha point, a method known as the lateral condensation method is usually conducted. This method utilizes two types of guttapercha points of different thickness from each other (a master point and an accessory point). The master point has a thickness which is the same as a reamer or a file which is used for the root canal preparation and is first filled in the root canal. The thin accessory point is then placed in the root canal under pressure in the gap between the root canal wall and the master point. In order to seal the inside of the root canal to a good state by the guttapercha points according to this method, it is necessary to minutely fill the root canal with the guttapercha points. However, since the guttapercha points have extremely low plasticity, it is difficult to completely seal the inside of the root canal. In the event the filling is incomplete, tissue fluid from the root apex is liable to penetrate into the root canal, resulting in inflammation. Also, depending on the case, the guttapercha points protrude out from the root apex, leading to the generation of inflammation. Moreover, in order to achieve lateral condensation, it is necessary to implant a few guttapercha points, so that the operation is very complicated.

In order to overcome the complication of the lateral condensation with guttapercha points, a method has been developed in which a root canal filling material having a relatively low softening temperature is heat softened and then a root canal is filled using a syringe, or the like. However, although the root canal filling material that is presently used for this method has a relatively low softening temperature, when filled in the root canal, it rapidly cools, which decreases its fluidity within an extremely short period of time. For this reason, the root canal filling material hardens before completely filling the root canal, and is thereby likely to result in incomplete filling. Also, drawback occurs which is the inside of the root canal cannot be completely sealed by the root canal filling material because of its low adhesion to the root canal wall and large heat shrinkage.

SUMMARY OF THE INVENTION

In order to overcome the above-described defects of the related art technologies, an object of this invention is to provide a root canal filling material for filling root canals after heat softening and which adheres to root canal walls and presents simple operability for filing. In order to attain these objectives, the present invention provides a root canal filling material whose characteristics are that it can be softened at a relatively low temperature, it is not readily hardened after softening, and that it provides a sufficient working time so that the filling operation can be carried out in a root canal.

As a result of study, a root canal filling material has now been discovered that has good adhesion to root canal walls, can be softened at a relatively low temperature (from about 40 to 70° C.), can be filled into a root canal leaving a sufficient working time after the softening and that has less shrinkage and sufficient hardness during hardening in the root canal.

Specifically, the root canal filling material according to the present invention is one in which polybutene and ester gum having a prescribed number average molecular weight are present in a guttapercha which is a natural resin generally used in guttapercha points and/or in trans-polyisoprene which is the major component of the guttapercha for the purpose of improving the adhesion of the material to a root canal wall while minimizing the shrinkage during hardening in a root canal. Further a paraffin wax is present for the purpose of lowering the viscosity after heat softening. Further one or more than two inorganic fillers selected from zinc oxide, barium sulfate and calcium hydroxide are present for the purpose of maintaining an adequate hardness of the filling material in the root canal.

More specifically, the invention is a root canal filling material comprising (A) from 1 to 50% by weight of guttapercha and/or trans-polyisoprene, (B) from 0.1 to 10% by weight of polybutene having a number average molecular weight of from 600 to 4,000, (C) from 0.1 to 10% by weight of ester gum, (D) from 0.1 to 20% by weight of paraffin wax, and (E) from 10 to 95% by weight of one or more than two inorganic fillers selected from zinc oxide, barium sulfate and calcium hydroxide.

DESCRIPTION OF THE PREFERRED EMBODIMENTS

The guttapercha and/or trans-polyisoprene as component (A) is the basic component of the root canal filling material according to the present invention and imparts the basic strength and moldability to the root canal filling material. Of these, guttapercha is a natural resin which contains various compounds as impurities; and the trans-polyisoprene is a resin that is the major component of the guttapercha and is prepared by synthesis and used in place of the natural guttapercha. It is necessary that component (A) be present in an amount of from 1 to 50% by weight in the root canal filling material according to the present invention. If the amount of component (A) is less than 1% by weight, not only is sufficient strength not imparted to the root canal filling material, but also the resulting product is very brittle, whereby the stability in the root canal is lowered. On the other hand, when the amount of component (A) exceeds 50% by weight, the viscosity during heat softening is too high, so that the filling operation becomes very difficult, and likely results in incomplete root canal filling. The amount of component (A) is preferably from 3 to 40% by weight. This is because the viscosity of the material during filling of the root canal in a heat softened state is proper in order to simplify the filling operation.

The polybutene having a number average molecular weight of from 600 to 4,000 as the component (B), when used together with the ester gum as component (C), can improve the adhesion to a root canal wall and has an effect for minimizing the shrinkage generated during filling in a root canal in a heat softened state. Further, it has an effect of prolonging the working time during heat softening and filling the root canal. The polybutene is a liquid polymer comprising isobutylene as the major component having a small amount of 1-butene copolymerized therewith and properly has a number average molecular weight of from 600 to 4,000. If the number average molecular weight of the polybutene is 600 or less, the tackiness is so low that the adhesion to the root canal wall is insufficient when used together with the component (C). Further, during filling of the root canal with filling material after heat softening, the fluidity is rapidly lost, which extremely shortens the time in which the filling operation can be conducted. On the other hand, if the number average molecular weight of the polybutene exceeds 4,000, during heat softening the root canal filling material, the viscosity becomes so high that the filling operation becomes difficult. The number average molecular weight of component (B) is preferably from 1,000 to 3,000. This is because not only is the fluidity of the material adequate, but also adhesion of the filling material to the root canal wall is good. If the amount of the polybutene is less than 0.1% by weight, the effects thereof are not sufficient. If the amount exceeds 10% by weight, the hardness of the root canal filling material is markedly lowered. The amount of component (B) is preferably from 1 to 5% by weight. This is because the adhesion to the root canal wall is sufficient, and even in case where the root canal filling material has to be removed after filling the root canal, it can be easily removed without being torn off on the way because it is properly hard.

The ester gum as component (C), when used together with the polybutene as component (B), has an effect of improving the adhesion of the filling material to the root canal wall and functions to minimize shrinkage of the filling material in the root canal after filling. As the ester gum as component (C) which is generally prepared by esterifying rosin with glycerin, the ester gum prepared by esterifying hydrogenated rosin with glycerin can also be used. If the amount of the ester gum is less than 0.1% by weight, the adhesion of the filling material to the root canal wall is not sufficient when used together with component (B). On the other hand, if the amount of the ester gum exceeds 10% by weight, the tackiness of the filling material is too high, such that where the root canal filling material has to be removed after filling a root canal, the removal becomes very difficult. The amount of component (C) is preferably from 1 to 5% by weight. This is because not only the adhesion to the root canal wall is sufficient, but also the actual filling operation can be readily carried out, since the resulting root canal filling material does not excessively stick to equipment used in the filling of root canals.

The paraffin wax as component (D) has the effect of lowering the viscosity of the filling material when it is heat softened. The paraffin wax as component (D), if used alone, decreases the viscosity of the filling material, but lowers adhesion to the root canal wall, thereby increasing significantly the extent of shrinkage of the filling material after heat softening. This drawback, however, can be overcome by the use of the above-described components (B) and (C). It is necessary that component (D) be present in an amount of from 0.1 to 20% by weight in the root canal filling material. If the amount of component (D) is less than 0.1% by weight, the viscosity after heat softening is so high that the filling operation becomes difficult. On the other hand, if the amount of component (D) exceeds 20% by weight, adhesion of the filling material to the root canal decreases. The amount of component (D) is preferably from 2 to 10% by weight. This is because the viscosity after heat softening can be properly lowered without impairing adhesion to the root canal wall within the ranges of the amounts of the components (B) and (C).

One or more than two inorganic fillers selected from zinc oxide, barium sulfate and calcium hydroxide as the component (E) has the effects of imparting hardness and roentgenopacity to the root canal filling material. In order to impart a proper hardness as the root canal filling material, the use of only the components (A) to (D) as described above is insufficient, and the use of the component (E) is necessary. Further, in order to confirm the state that the root canal filling material fills in the root canal, confirmation by roentgen ray imaging is necessary. For this purpose, the root canal filling material must have a roentgenopacity. Any of zinc oxide, barium sulfate and calcium hydroxide have a roentgenopacity and adequate amounts of component (E) range from 10 to 95% by weight. If the amount of component (E) is less than 10% by weight, not only the hardness of the root canal filling material is low, but also its roentgenopacity is so insufficient that confirmation by roentgen ray imaging cannot be substantially performed. On the other hand, if the amount of component (E) exceeds 95% by weight, not only is the resulting root canal filling material too brittle, but also its fluidity during filling of the root canal after heat softening is extremely diminished which results in deterioration of the filling operation. The amount of component (E) preferably ranges from 50 to 87% by weight. This is because not only is the confirmation by roentgen ray imaging made easy, but also the viscosity of the root canal filling material after heat softening is adequate so that the work involved for filling the root canal with filling material is easy.

In the root canal filling material according to the present invention, so far as its characteristics are not impaired, various inorganic and/or organic colorants can be used.

The root canal filling material according to the present invention is described in more detail with reference to the following Examples, but it should not be construed that the present invention is limited thereto.

EXAMPLES

Example 1

| | |
|---|---|
| Trans-polyisoprene | 10% by weight |
| Polybutene (number average molecular weight: 2,900) | 5% by weight |
| Ester gum (glycerin ester of rosin) | 5% by weight |
| Paraffin wax | 10% by weight |
| Zinc oxide | 70% by weight |

The above-described components were weighed and kneaded by a pressure kneader under conditions of 110 to 120° C. to prepare a root canal filling material. The thus prepared root canal filling material was tested for adhesion, working time and pressure contraction rate (at 37° C.). The results are shown in Table 1.

A) Adhesion

The root canal filling material was heated at 70° C. and a glass tube having an inside diameter of 2 mm and a length of 20 mm was filled with the material, which was then immersed in a 0.6% Rhodamine aqueous solution in a chamber at 37° C. After immersion, the length of coloring matter which penetrates into the glass tube was measured and evaluated under the following criterion. That is, a length of 2 mm or less is good, and a length exceeding 2 mm is bad.

B) Working time

A transparent acrylic resin block was drilled with a cone-shaped hole which is like root canal having a depth of 15 mm by using H file #25 and allowed to stand in a chamber at 37° C. The root canal filling material was heated at 70° C. and the cone-shaped hole in the acrylic resin block at 37° C. was filled using a lenticule. The maximum time during which the filling operation could be carried out was measured.

C) Pressure contraction rate

The pressure contraction rate at 37° C. was measured in accordance with JIS T 6504 "Dental Impression Compound". The smaller the measured value, the harder the root canal filling material, i.e. it is difficult to deform at 37° C.

Example 2

| | |
|---|---|
| Trans-polyisoprene | 4.4% by weight |
| Polybutene (number average molecular weight: 3,700) | 0.2% by weight |
| Ester gum (glycerin ester of rosin) | 0.2% by weight |
| Paraffin wax | 0.2% by weight |
| Zinc oxide | 60% by weight |
| Barium sulfate | 35% by weight |

The above-described components were weighed and kneaded by a pressure kneader under conditions of 110 to 120° C. to prepare a root canal filling material. The thus prepared root canal filling material was tested in the same manner as described in Example 1. The results are summarized in Table 1.

Example 3

| | |
|---|---|
| Trans-polyisoprene | 50% by weight |
| Polybutene (number average molecular weight: 1,000) | 10% by weight |
| Ester gum (glycerin ester of hydrogenated rosin) | 10% by weight |
| Paraffin wax | 20% by weight |
| Zinc oxide | 10% by weight |

The above-described components were weighed and kneaded by a pressure kneader under conditions of 110 to 120° C. to prepare a root canal filling material. The thus prepared root canal filling material was tested in the same manner as described in Example 1. The results are summarized in Table 1.

Example 4

| | |
|---|---|
| Trans-polyisoprene | 4% by weight |
| Polybutene (number average molecular weight: 1,400) | 4% by weight |
| Ester gum (glycerin ester of rosin) | 4% by weight |
| Paraffin wax | 4% by weight |
| Zinc oxide | 84% by weight |

The above-described components were weighed and kneaded by a pressure kneader under conditions of 110 to 120° C. to prepare a root canal filling material. The thus prepared root canal filling material was tested in the same manner as described in Example 1. The results are summarized in Table 1.

Comparative Example 1

| | |
|---|---|
| Guttapercha | 15% by weight |
| Zinc oxide | 85% by weight |

The above-described components were weighed and kneaded by a pressure kneader under conditions of 110 to 120° C. to prepare a root canal filling material. The thus prepared root canal filling material was tested in the same manner as described in Example 1. The results are summarized in Table 1.

Comparative Example 2

| | |
|---|---|
| Guttapercha | 10% by weight |
| Paraffin wax | 10% by weight |
| Zinc oxide | 80% by weight |

The above-described components were weighed and kneaded by a pressure kneader under conditions of 110 to 120° C. to prepare a root canal filling material. The thus prepared root canal filling material was tested in the same manner as described in Example 1. The results are summarized in Table 1.

Comparative Example 3

A few glass tubes were filled with GC Guttapercha Points (GC Corporation) in order to conduct the adhesion test as described as minute as possible. The filled tubes were then subjected to the adhesion test in the same manner as described in Example 1. Also, the pressure contraction rate was tested in the same manner as described in Example 1. The results are summarized in Table 1.

Comparative Example 4

| | |
|---|---|
| Guttapercha | 10% by weight |
| Polybutene (number average molecular weight: 1,400) | 20% by weight |
| Zinc oxide | 70% by weight |

The above-described components were weighed and kneaded by a pressure kneader under conditions of 110 to 120° C. to prepare a root canal filling material. The thus prepared root canal filling material was tested in the same manner as described in Example 1. The results are summarized in Table 1.

TABLE 1

| | Example No. | | | | Comparative Example No. | | | |
|---|---|---|---|---|---|---|---|---|
| | 1 | 2 | 3 | 4 | 1 | 2 | 3 | 4 |
| Adhesion | Good | Good | Good | Good | Bad | Bad | Bad | Bad |
| Working Time | 3 min. | 2 min. | 4 min. | 3 min. | 10 sec. | 30 sec. | — | 3 min. |
| Pressure contraction rate (%) | 4.5 | 3.9 | 6.3 | 4.2 | 3.7 | 5.2 | 4.2 | 60.0 |

As is clear from Table 1, it has been confirmed that the root canal filling material according to the present invention exhibits good adhesion and provides a sufficient working time after heat softening as long as from 2 to 4 minutes for carrying out the actual root canal filling. Further, the pressure contraction rate at 37° C. ranges from 3.9 to 6.3%, which is a value which is substantially the same as the pressure contraction rate (4.2%) of Comparative Example 3 regarding the presently used guttapercha point, i.e., the root canal filling material according to the present invention has a sufficient hardness in the root canal. On the other hand, in both of Comparative Example 1 in which the root canal filling material is prepared from only guttapercha and zinc oxide and Comparative Example 2 in which the root canal filling material is prepared from guttapercha, paraffin wax and zinc oxide, the adhesion was inferior, and the working time after heat softening was very short. Further, in Comparative Example 4, the working time after heat softening was sufficient because polybutene is present. However, since the content of polybutene is too high as compared with that in the root canal filling material according to the present invention, the hardness after cooling was low, and the pressure contraction rate at 37° C. was very high as 60%, meaning that the composition is inadequate for use as a root canal filling material. Moreover, the adhesion was inferior.

As described above in detail, the root canal filling material according to the present invention has high adhesivity to root canal walls and provides a sufficient working time after heat softening so that the filling operation can be simply carried out with an enough time to spare. Thus, the characteristics that have hitherto been considered to be defects of root canal filling material for the filling of root canals upon heat softening can be remarkably improved so that the present invention will greatly contribute to the dental field.

While the invention has been described in detail and with reference to specific embodiments thereof, it will be apparent to one skilled in the art that various changes and modifications can be made therein without departing from the spirit and scope thereof.

What is claimed as new and is intended to be secured by Letters Patent is:

1. A root canal filling material comprising:
   (A) from 1 to 50%, by weight of guttapercha and/or trans-polyisoprene;
   (B) from 0.1 to 10%, by weight of polybutene having a number average molecular weight of from 600 to 4,000;
   (C) from 0.1 to 10%, by weight of ester gum;
   (D) from 0.1 to 20%, by weight of paraffin wax; and
   (E) from 10 to 95% by weight of at least one inorganic fillers selected from the group consisting of zinc oxide, barium sulfate and calcium hydroxide.

* * * * *